(12) United States Patent
Hashimoto et al.

(10) Patent No.: US 7,232,413 B2
(45) Date of Patent: Jun. 19, 2007

(54) PULSE WAVE MEASURING APPARATUS

(75) Inventors: Masao Hashimoto, Kyoto (JP);
Kazunobu Itonaga, Kyoto (JP);
Tomoki Kitawaki, Okayama (JP);
Kazuhisa Tanabe, Kyoto (JP); Ryo Fukui, Kadoma (JP); Hironori Sato, Moriyama (JP)

(73) Assignee: Omron Healthcare Co., Ltd., Kyoto (JP)

( * ) Notice: Subject to any disclaimer, the term of this patent is extended or adjusted under 35 U.S.C. 154(b) by 287 days.

(21) Appl. No.: 10/758,600

(22) Filed: Jan. 16, 2004

(65) Prior Publication Data
US 2004/0193062 A1  Sep. 30, 2004

(30) Foreign Application Priority Data
Jan. 23, 2003 (JP) ............................. 2003-014412
Sep. 17, 2003 (JP) ............................. 2003-324925

(51) Int. Cl.
*A61B 5/02* (2006.01)
(52) U.S. Cl. ...................................... 600/500; 600/485
(58) Field of Classification Search ........ 600/500–503, 600/485
See application file for complete search history.

(56) References Cited

U.S. PATENT DOCUMENTS

| | | | | |
|---|---|---|---|---|
| 4,409,983 | A | * | 10/1983 | Albert ......................... 600/503 |
| 5,494,043 | A | * | 2/1996 | O'Sullivan et al. .......... 600/500 |
| 5,595,180 | A | * | 1/1997 | Ogura et al. ................. 600/499 |
| D406,346 | S | * | 3/1999 | Hirakawa .................... D24/165 |
| 6,132,383 | A | | 10/2000 | Chesney et al. |
| 6,544,188 | B1 | * | 4/2003 | Chesney et al. ............. 600/500 |
| 6,932,772 | B2 | * | 8/2005 | Kan ............................ 600/490 |
| 2002/0120199 | A1 | * | 8/2002 | Ogura et al. ................. 600/485 |
| 2003/0004421 | A1 | | 1/2003 | Ting et al. |
| 2004/0010199 | A1 | * | 1/2004 | Hashimoto et al. ......... 600/502 |

FOREIGN PATENT DOCUMENTS

| | | |
|---|---|---|
| EP | 1 177 762 A1 | 2/2002 |
| EP | 1 360 930 A1 | 11/2003 |
| JP | 11-70087 A | 3/1999 |

OTHER PUBLICATIONS

Extended European Search Report dated Sep. 26, 2005, directed to corresponding EP Application No. 05014837.8.

* cited by examiner

*Primary Examiner*—Charles A. Marmor, II
*Assistant Examiner*—Karen E Toth
(74) *Attorney, Agent, or Firm*—Morrison & Foerster LLP

(57) ABSTRACT

A pulse wave measuring apparatus is disclosed, in which a sensor unit can be fixed easily under an appropriate pressure at an appropriate position on a living organism. With the living organism fixed by a living organism fixing device, a pressure sensitive portion arranged on the sensor unit is pressed against the living organism thereby to measure the pulse wave. The living organism fixing device includes a fixing stand for fixing the living organism in position, and fastening bands for connecting the fixing stand and the sensor unit and fastening the living organism fixedly to the fixing stand while at the same time activating by pressing the sensor unit against the living organism. The fastening bands include a first band portion with one end mounted on the sensor unit and the other end mounted on the fixing stand and a second band portion with one end mounted on the sensor unit and the other end removably mounted on the fixing stand. The fixing stand has a constant force spring for pulling the other end of the first band portion with a constant force.

13 Claims, 16 Drawing Sheets

PRIOR ART

PULSE WAVE MEASURING APPARATUS

BACKGROUND OF THE INVENTION

1. Field of the Invention

The present invention relates to a pressure-type pulse wave measuring apparatus for measuring the pulse wave by pressing a pressure sensitive portion against a living organism, or in particular to a pressure-type pulse wave measuring apparatus having a fixing stand for fixing the living organism in position.

2. Description of the Related Art

A pressure-type pressure measuring apparatus for measuring the contact pressure with an object of measurement by pressing the particular object is generally known. An application of the pressure-type pressure measuring apparatus is a pulse wave measuring apparatus. With this pulse wave measuring apparatus, the pulse wave generated from the artery located at a comparatively shallow position of the skin of a living organism is measured by pressing a board having a pressure sensitive part on the surface of the living organism. Measuring the pulse wave of a subject using this pulse wave measuring apparatus is very critical to know the health of the subject.

The pressure-type pulse wave measuring apparatus generally uses a semiconductor pressure detector having a distortion gauge or a diaphragm as a pressure sensitive part. In such a case, a pressure sensitive unit is configured in such a manner that the pressure sensitive part for detecting the pulse wave is located on the surface of a sensor unit mounted on the living organism.

In the pulse wave measuring apparatus having the configuration described above, the sensor unit is required to be activated by being mounted at an appropriate position on the living organism under an appropriate magnitude of pressure. A fastening band is generally used for mounting the sensor unit on the living organism. The fastening band is required to be mounted on the living organism with an appropriate fastening force not to give the subject any pain.

A pulse wave measuring apparatus realizing this appropriate fastening force is disclosed in Japanese Unexamined Patent Publication No. 3-146027 (patent document 1). The pulse wave measuring apparatus disclosed in this patent publication is explained below with reference to FIG. 15.

FIG. 15 is a longitudinal sectional view of a pulse wave measuring apparatus disclosed in the aforementioned patent publication. In the pulse wave measuring apparatus shown in FIG. 15, the wrist is used as an object portion for measuring the pulse wave of the subject.

As shown in FIG. 15, the pulse wave measuring apparatus comprises, as main components, a sensor unit 140 having a pressure sensitive unit, an engaging portion 162 arranged adjacently to the sensor unit 140, a fastening band 130 mounted on the sensor unit 140 through a fitting 164, and a tension adjusting part 166 mounted on the other end of the fastening band 130. A fixing part such as a hook-and-loop fastener (not shown) is arranged on the upper surface of the engaging portion 162 and the inner peripheral surface of the fastening band 130.

The tension adjusting part 166 is configured of a holding member 167 secured to the fastening band 130, a grip member 168 mounted slidably on the holding member 167 along the longitudinal direction of the fastening band 130, and a coil spring (not shown) for connecting the holding member 167 and the grip member 168.

The pulse wave measuring apparatus having the structure described above is mounted on a living organism in the manner described below. First, the sensor unit 140 is set on the wrist 151 in such a position that the pressure sensitive portion is located just above the radial artery 153. Under this condition, the fastening band 130 is wound around the wrist 151 of the subject. In the process, the fastening band 130 is not held but the holding member 168 of the tension adjusting part 166, and wound on the wrist 151 while keeping the fastening band 130 pulled outward along the length thereof. The engaging portion 162 and the fastening band 130 are fixed by a fixing part not shown.

By use of the tension adjusting part 166 as described above, the fastening band 130 can be wound around the wrist 151 under a predetermined pressure range. This is by reason of the fact that a predetermined range of tension is imparted on the other end of the fastening band 130 through the holding member 167 with the elastic deformation of the coil spring by pulling the grip member 168 longitudinally of the fastening band 130. The employment of the aforementioned structure, therefore, makes it always possible to reproduce the state in which the sensor unit is kept activated by being pressed on the wrist under an appropriate pressure.

A pulse wave measuring apparatus with the sensor unit mountable at an appropriate position on the wrist is disclosed, for example, in Japanese Unexamined Utility Model Publication No. 3-67606 (patent document 2), Japanese Unexamined Patent Publication No. 5-261074 (patent document 3) and Japanese Unexamined Patent Publication No. 11-33007 (patent document 4). The pulse wave measuring apparatuses disclosed in these patent publications have a fixing unit for fixing the wrist position, by use of which the wrist of the subject is fixed in position before the sensor unit is mounted. The use of the fixing unit stabilizes the wrist position and therefore makes it possible to mount the sensor unit at an accurate position just above the artery.

The problem of the pulse wave measuring apparatus disclosed in patent document 1, however, is that the job of winding the fastening band on the wrist following the above-mentioned procedure is so complicated that it is very difficult to mount the apparatus correctly.

With the pulse wave measuring apparatus disclosed in patent document 1, the fastening band is required to be wound entirely around the wrist. Also, in view of the fact that the wrist size is varied from one subject to another, the length of the fastening band is required to have some margin. This considerably lengthens the fastening band, and the job of winding this long fastening band by pulling it by an end thereof along longitudinally outward is very bothersome.

Also, when mounting the pulse wave measuring apparatus disclosed in patent document 1 on a living organism, it is always necessary to wind the fastening band on the wrist by holding only the grip member of the tension adjusting part. In the process, the grip member is required to be pulled with such a force as to generate the elastic deformation of the coil spring to obtain an appropriate tension at an end of the fastening band. The degree of tension to be applied is left up to the user, and an excessively small tension would loosen or twist the fastening band, thereby making it impossible to obtain an appropriate fastening force. An excessively large tension, on the other hand, would cause so strong a tension in the sensor unit that the sensor unit would be displaced from the predetermined position just over the artery. It is therefore very difficult and a complicated job is required on the part of the user to apply an appropriate fastening force to the fastening band by manual adjustment of the tension.

For the reason described above, the user may go so far as to wind the fastening band on the wrist directly by holding it in hand without following the above-mentioned procedure. In the case where the apparatus is mounted this way, however, an appropriate fastening force is not obtained and it is difficult to the measure the pulse wave accurately.

In the pulse wave measuring apparatuses disclosed in patent documents 2 to 4 described above, on the other hand, the fastening band cannot be easily wound with an appropriate fastening force although the sensor unit can be mounted at an appropriate position. Thus, the sensor unit cannot be activated by being pressed with an appropriate force against a living organism.

SUMMARY OF THE INVENTION

Accordingly, it is an object of this invention to solve the aforementioned problems and provide a pulse wave measuring apparatus having a fixing stand for fixing the wrist in position, in which the sensor unit can be easily fixed at an appropriate position on a living organism under an appropriate pressure.

According to this invention, there is provided a pulse wave measuring apparatus comprising a sensor unit having a pressure sensitive portion and a fixing device for fixing a living organism, wherein the pulse wave is measured by pressing the pressure sensitive portion against the living organism fixed by the fixing device. The living organism fixing device includes a fixing stand for fixing the living organism in position, and a fastening band for connecting the fixing stand and the sensor unit to each other and fastening the living organism fixedly on the fixing stand, while at the same time activating by pressing the sensor unit against the living organism. The fastening band includes a first band portion with one end thereof mounted on the sensor unit and the other end thereof mounted on the fixing stand, and a second band portion with one end thereof mounted on the sensor unit and the other end thereof removably mounted on the fixing stand. The fixing stand has a tensioning part for pulling the other end of the first band portion with a predetermined force.

The tensioning part arranged on the fixing stand for pulling the other end of the first band portion of the fastening band with a predetermined force greatly facilitates the job of mounting the pulse wave measuring apparatus. Specifically, once the sensor unit is set in position on the living organism, no matter how the fastening band is wound on the living organism, the other end of the first band portion of the fastening band is pulled always under a predetermined tension and therefore always fastened with an appropriate fastening force. As a result, the sensor unit can be mounted easily in activated state under an appropriate pressure at an appropriate position on the living organism. Thus, the pulse wave can be measured accurately in stable manner. Also, since the fastening band is pulled always under a constant tension, the sensor unit is less likely to be displaced.

The pulse wave measuring apparatus according to this invention preferably further comprises a fixing part for fixing the first band portion on the fixing stand relatively immovably, for example, with the other end of the second band portion mounted on the fixing stand.

The aforementioned configuration in which the first band portion is fixed on the fixing stand relatively immovably with the other end of the second band portion mounted on the fixing stand brings the fastening band and the object portion of the subject into closer contact with each other. Should the subject move the object portion, therefore, the fastening band is not loosened. As a result, the sensor unit is not displaced, and the pulse wave can be measured accurately in more stable manner.

Preferably, with the pulse wave measuring apparatus according to this invention, the fixing part, for example, is configured of a hook-and-loop fastener arranged on the first and second band portions, and by engaging the first band portion and the second band portion each other by the hook-and-loop fastener, the first band portion is fixed on the fixing stand relatively immovably.

By fixing the first band portion and the second band portion directly as described above, the living organism including the object portion is fastened over the entire circumference by the fastening band. Thus, the fastening band and the object portion of the subject are brought into closer contact with each other and the fastening band is not easily loosened. As a result, the pulse wave can be measured accurately in more stable manner. Also, the use of the hook-and-loop fastener makes it possible to freely adjust the position at which the second band portion is mounted on the fixing stand. This not only further improves the tightness but leads to a greater handling ease.

Preferably, with the pulse wave measuring apparatus according to this invention, the one end of the first band portion engages the other end of the second band portion and the other end of the first band portion engages the one end of the second band portion at a position where the first band portion and the second band portion engage each other by the hook-and-loop fastener.

With this configuration, the first band portion is not moved with the second band portion when disengaging the first and second band portions from each other, i.e. when pulling off the second band portion from the first band portion by holding the second band portion. Thus, the second band portion smoothly comes off from the first band portion. As a result, the handling ease is improved.

Preferably, with the pulse wave measuring apparatus according to the invention, the fixing part, for example, is configured of a brake member operatively interlocked with the process of mounting the second band portion on the fixing stand. By mounting the second band portion on the fixing stand, therefore, the brake member comes into contact with the first band portion so that the first band portion is fixedly pressed on the fixing stand relatively immovably.

As described above, the first band portion is fixedly pressed on the fixing stand relatively immovably by the brake member in an operatively interlocked relation with the process of fixing the second band portion on the fixing stand. Thus, the fastening band is not easily loosened with the sensor unit mounted, thereby making it possible to measure the pulse wave accurately in stable fashion.

Preferably, with the pulse wave measuring apparatus according to this invention, the tensioning part, for example, is accommodated in the fixing stand, and the first band portion includes an internal part accommodated in the fixing stand and an external part not accommodated in the fixing stand but arranged outside the fixing stand. In the state in which the living organism is not fixed by the living organism fixing device, the first band portion is guided relatively movably with respect to the fixing stand by a guide part arranged in the fixing stand.

The apparatus can be reduced in size by arranging the tensioning part in the fixing stand as described above. Also, with the tensioning part arranged in the fixing stand, the first band portion is partially located in the fixing stand. The configuration in which the accommodated part of the first band portion is guided by the guide part in the fixing stand, however, permits the fastening band to be pulled in and out smoothly for an improved operability.

Preferably, with the pulse wave measuring apparatus according to this invention, the guide part, for example, is configured of at least a roller arranged on the sliding parts of the fixing stand and the first band portion.

By configuring the guide part of at least a roller as described above, the fastening band can be pulled in and out more smoothly for a further improved operability.

Preferably, the pulse wave measuring apparatus according to this invention further comprises a band length adjusting part for adjusting the length of the unaccommodated part of the first band portion.

This configuration makes it possible to maintain the proper length of the unaccommodated part of the first band portion arranged outside the fixing stand in accordance with the size of the object portion of the subject, and therefore the sensor unit can be mounted at an appropriate position.

Preferably, with the pulse wave measuring apparatus according to this invention, the band length adjusting part, for example, is arranged on the unaccommodated part of the first band portion.

The fact that the band length adjusting part for adjusting the length of the fastening band is arranged on the unaccommodated part of the first band portion makes it possible to adjust the length of the unaccommodated part of the first band portion easily for an improved convenience.

Preferably, with the pulse wave measuring apparatus according to this invention, the band length adjusting part, for example, is arranged on the fixing stand.

This configuration in which the band length adjusting part for adjusting the length of the fastening band is arranged on the unaccommodated part of the first band portion makes it possible to adjust the length of the unaccommodated part of the first band portion easily for an improved convenience, while at the same time reducing the size of the apparatus.

Preferably, with the pulse wave measuring apparatus according to this invention, the band length adjusting part, for example, further includes a band length maintaining part for maintaining a predetermined length of the unaccommodated part of the first band portion after adjustment.

The provision of the band length maintaining part makes it possible to adjust the length of the unaccommodated part of the first band portion only when desired. As a result, the fastening band is not loosened by the unintentional length adjustment of the unaccommodated part of the first band portion by the band length adjusting part with the sensor unit mounted. Thus, the pulse wave can be measured accurately in stable fashion.

Preferably, with the pulse wave measuring apparatus according to this invention, the band length adjusting part, for example, is configured of a rotary member with one end journalled and the other end rotatable. The first band portion slidably engages the fixed shaft and the movable shaft arranged at the one end and the other end, respectively, of the rotary member, so that the length of the unaccommodated part of the first band portion is adjusted by rotating the rotary member.

One example configuration of the band length adjusting part arranged in the fixing stand uses the rotary member described above. This configuration permits the band length of the first band portion located outside the fixing stand to be adjusted in accordance with the size of the object portion of the subject by rotating the rotary member by a predetermined amount.

Preferably, with the pulse wave measuring apparatus according to this invention, the tensioning part, for example, is a constant force spring.

The use of a constant force spring as the tensioning part makes it possible to always generate a predetermined tension at the other end of the first band portion with a comparatively simple configuration.

According to this invention, the sensor unit can be easily fixed under an appropriate pressure at an appropriate position on a living organism. Thus, not only the pulse wave can be accurately and stably measured but also the user convenience is improved at the same time.

DESCRIPTION OF THE PREFERRED EMBODIMENTS

Embodiments of this invention are explained below with reference to the accompanying drawings. The embodiments described below represent a pulse wave measuring apparatus, as an example, using the wrist as an object portion through which the pulse wave of a subject is measured.

First Embodiment

Figure 1:
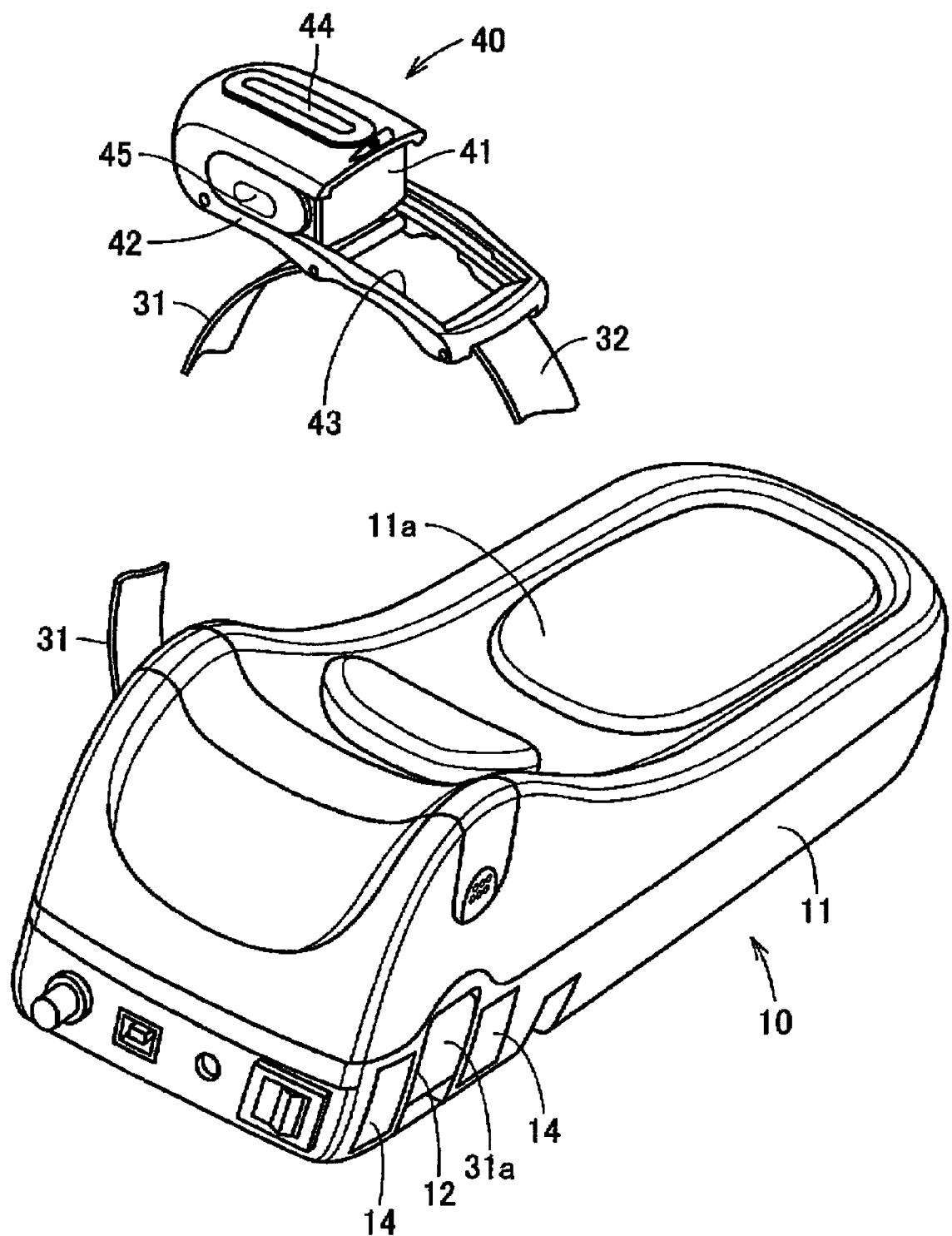
FIG. 1 shows a schematic perspective view of the general configuration of a pulse wave measuring apparatus according to a first embodiment of the invention.
Figure 2:
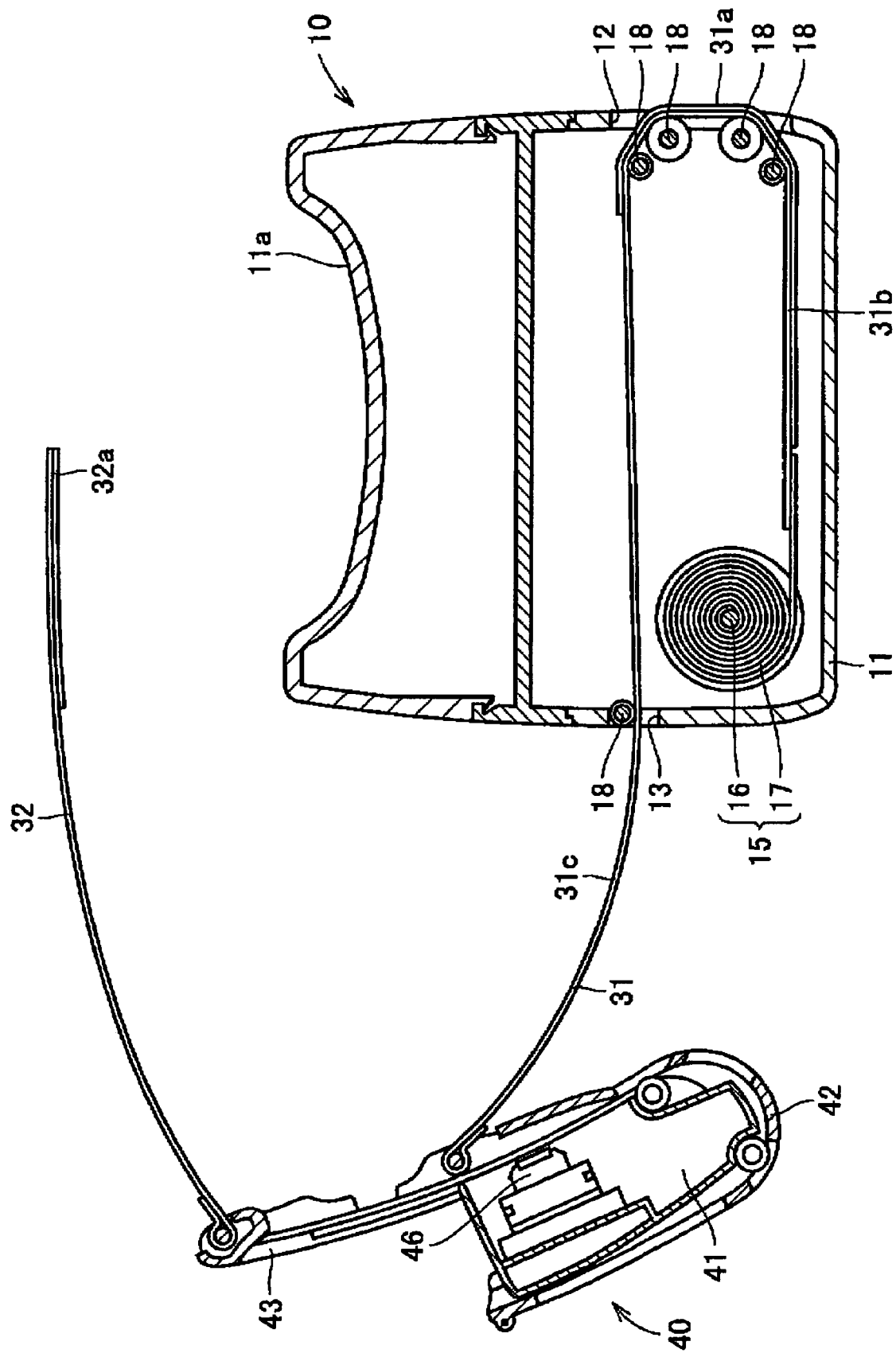
FIG. 2 shows a schematic longitudinal sectional view of a pulse wave measuring apparatus according to the first embodiment of the invention.

FIG. 1 is a perspective view schematically showing the general configuration of a pulse wave measuring apparatus according to a first embodiment of the invention. FIG. 2 is a longitudinal sectional view schematically showing the pulse wave measuring apparatus of FIG. 1.

As shown in FIGS. 1 and 2, the pulse wave measuring apparatus according to this embodiment comprises a sensor unit 40, and a fixing stand 10 and fastening bands 31, 32 as a living organism fixing device. As shown in FIG. 2, the fixing stand 10 and the sensor unit 40 are connected by the fastening bands 31, 32. The fastening bands include a first band portion 31 with one end thereof mounted on the sensor unit 40 and the other end thereof mounted on the fixing stand 10, and a second band portion 32 with one end thereof mounted on the sensor unit 40 and the other end thereof removably mounted on the fixing stand 10. Each band portion has an appropriate flexibility.

As shown in FIG. 1, the fixing stand 10 is configured of a resin housing 11 having a depression 11a on the upper surface thereof, and in operation, used on a horizontal table such as a desk. The depression 11a is so shaped as to accommodate the arm between the elbow and the wrist. The subject places the arm in the depression 11a at the time of measurement, so that the wrist constituting an object portion is fixedly set in position.

An operating button and an output terminal are arranged on the front surface of the fixing stand 10. The output terminal is to transmit the pulse wave data detected by the pulse wave measuring apparatus to an arithmetic processing terminal such as an external personal computer (PC).

Also, as shown in FIG. 2, one of the side surfaces of the fixing stand 10 has an opening 13 through which the first band portion 31 is pulled out. The other side surface of the fixing stand 10 is formed with an opening 12. In an unfixed state of the apparatus (a state in which the wrist is not fixed by the living organisms fixing device), the first band portion 31 is partly exposed through the opening 12. Incidentally, a hook-and-loop fastener 14 (FIG. 1) is attached in a predetermined side surface area adjoining the opening 12 of the fixing stand 10. Also, a hook-and-loop fastener 31a is attached on the surface of that part of the first band portion 31 which is exposed through the opening 12 in the state pulled to the maximum from the state taken up by the tensioning part described later.

A constant force spring 15 providing the tensioning part is arranged in the housing 11 of the fixing stand 10. The constant force spring is defined as a spring including a long spring plate 17 bent with a predetermined radius of curvature and wound on a shaft 16, in which the return force generated when the forward end of the spring plate 17 is extended linearly is constant for any length of extension.

The other end of the first band portion 31 inserted through the opening 13 is fixed at the forward end of the spring plate 17. When the first band portion 31 is pulled, therefore, the other end of the first band portion 31 is kept pulled under a predetermined tension by the constant force spring 15.

The first band portion 31 is divided into an accommodated part 31b located in the fixing stand 10 and an unaccommodated part 31c located outside the fixing stand 10. The fixing stand 10 has therein a plurality of rollers 18 constituting a guide part for guiding the accommodated part 31b of the first band portion 31. The rollers 18 makes it possible to pull the first band portion 31 in and out of the fixing stand 10 smoothly.

As shown in FIG. 1, the sensor unit 40 includes a case 41 having a pressure sensitive portion 46 (FIG. 2) and a base 42 for supporting the case 41. The case 41 is adapted to slide along the length of the fastening bands 31, 32 on the rails laid on the base 42. Specifically, the case 41 is slidable between a position (standby position) where the opening 43 formed in the base 42 is closed and a position (accommodated position) where the opening 43 of the base 42 is not closed. FIG. 1 shows a state in which the case 41 is located in the accommodated position. The case 41 is slid by being moved while pressing the disengage button 45 arranged on the side of the case 41.

The opening 43 is formed so as to allow the pressure sensitive portion 46 arranged in the case 41 to be pressed against the wrist constituting the object portion. Thus, the pressure sensitive portion 46 moves down through the opening 43 and can be pressed against the wrist thereby making possible the measurement of the pulse wave. A display unit 44 for indicating whether the pressure sensitive portion 46 is set in position or not at the time of measurement is arranged on the upper surface of the sensor unit 40.

As described above, the first band portion 31 and the second band portion 32 providing fastening bands are mounted at predetermined positions on the base 42 of the sensor unit 40 on both sides of the opening 43. A hook-and-loop fastener 32a (FIG. 2) is attached on the inner peripheral surface at the tip of the other end of the second band portion 32.

Figure 3:
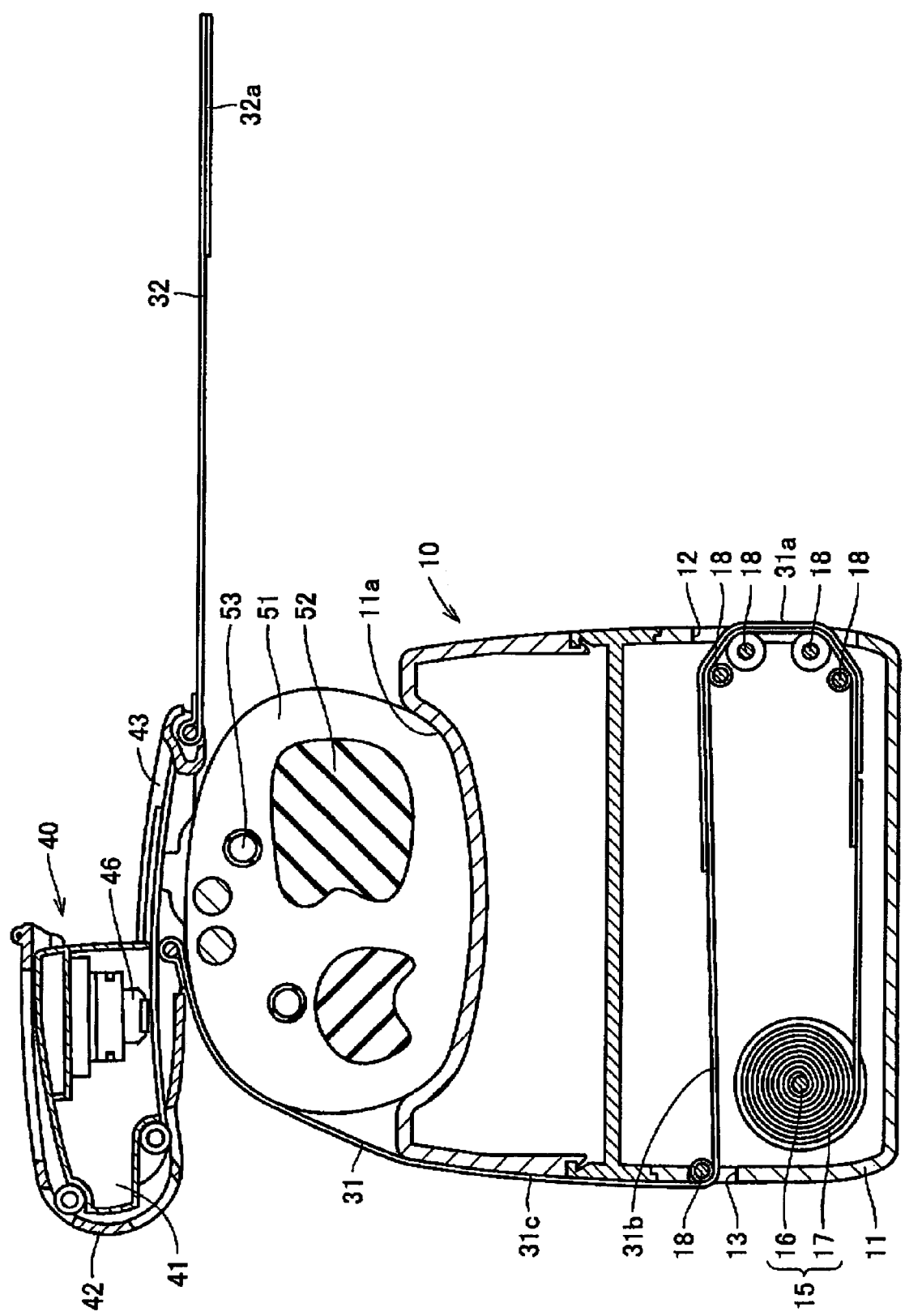
FIG. 3 shows a schematic longitudinal sectional view for explaining the process of mounting a pulse wave measuring apparatus according to the first embodiment of the invention.
Figure 4:
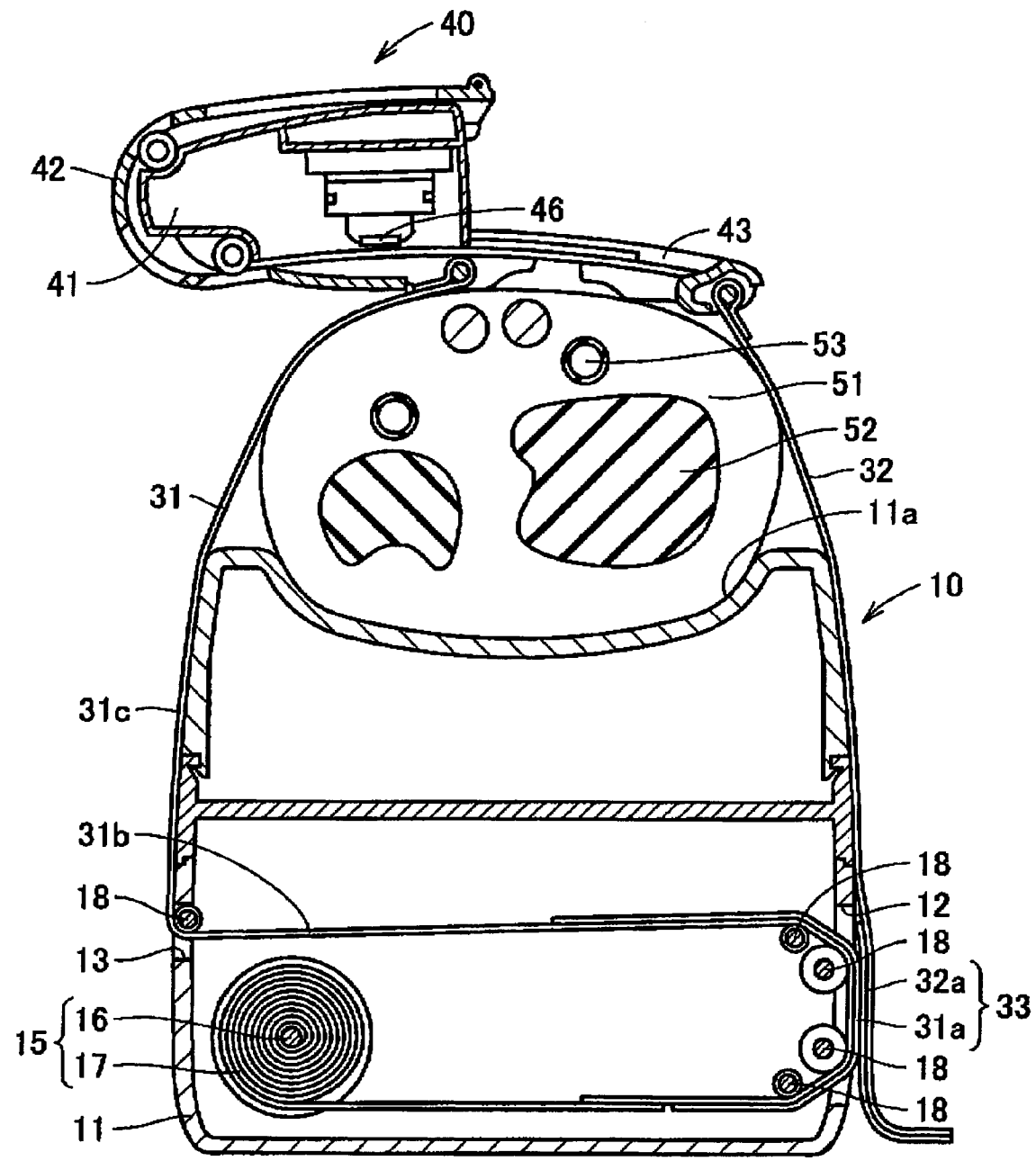
FIG. 4 shows a schematic longitudinal sectional view for explaining the process of mounting a pulse wave measuring apparatus according to the first embodiment of the invention.
Figure 5:
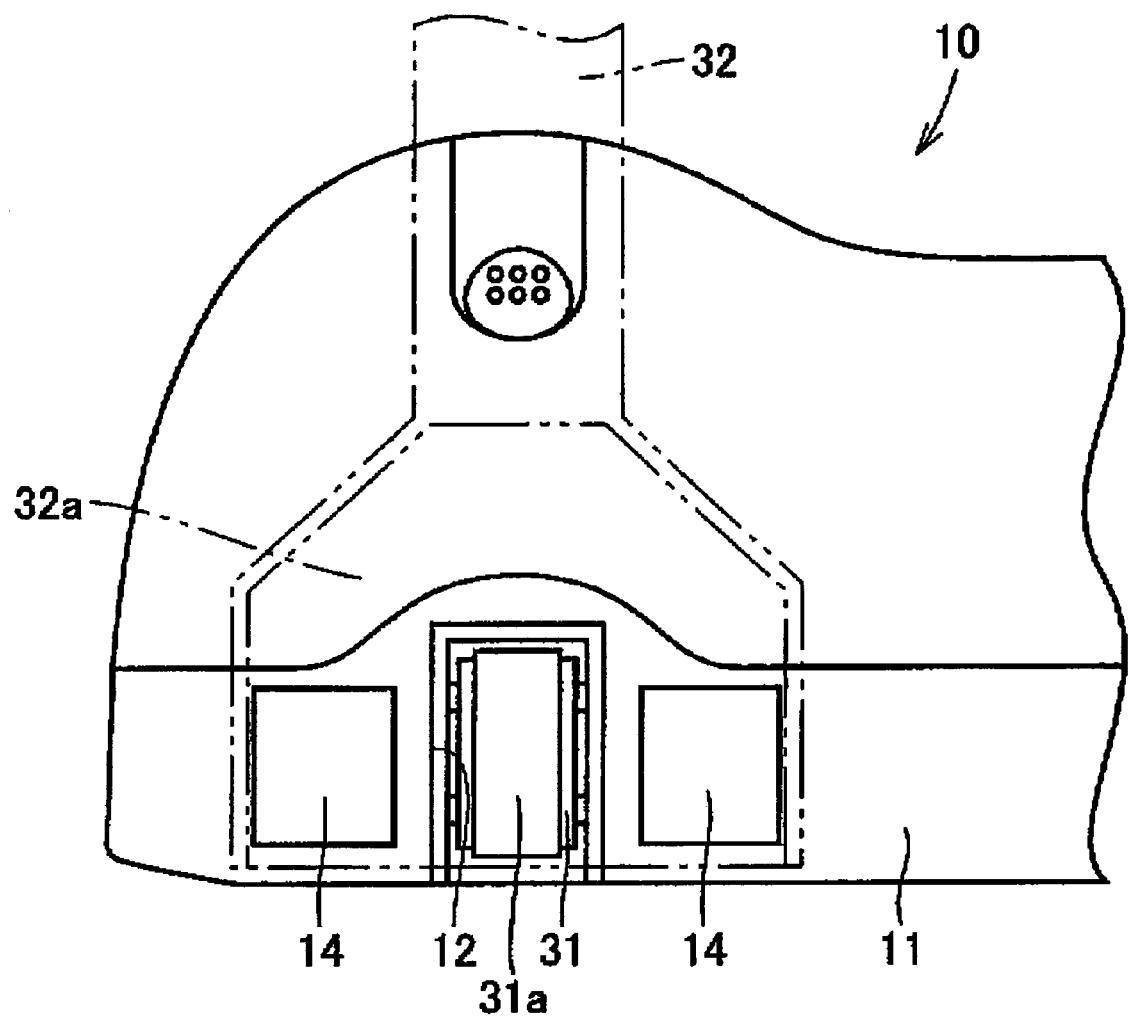
FIG. 5 shows a partial side view of the structure of the fixing part of a pulse wave measuring apparatus according to the first embodiment of the invention.
Figure 6:
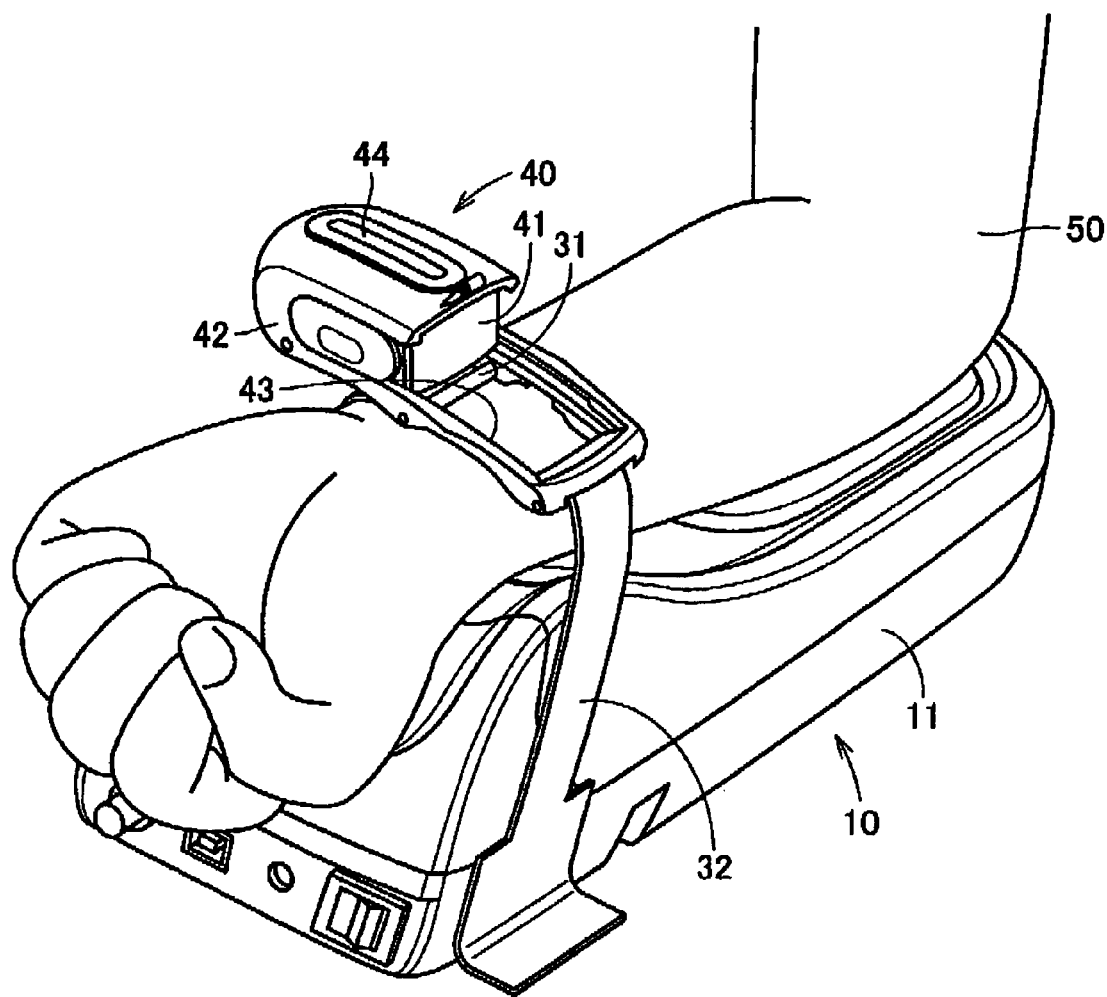
FIG. 6 shows a schematic perspective view of the mounted state of a pulse wave measuring apparatus according to the first embodiment of the invention.

FIGS. 3 and 4 are longitudinal sectional views showing the process of mounting the pulse wave measuring apparatus according to this embodiment. FIG. 5 is a partial side view showing the configuration of the fixing part of the pulse wave measuring apparatus according to this embodiment. Further, FIG. 6 is a perspective view schematically showing the pulse wave measuring apparatus according to this embodiment as mounted on the subject.

Referring to FIGS. 3 to 6, the description that follows deals with the process of mounting the pulse wave measuring apparatus according to this embodiment and the configuration after the same apparatus is mounted.

First, the arm extending from the elbow to the wrist is placed in the depression 11a formed in the upper surface of the housing 11 of the fixing stand 10. In the process, as shown in FIG. 3, care is taken to arrange the wrist 51 of the subject in a position corresponding to the first band portion 31 of the fastening bands pulled out of the fixing stand 10. As a result, the wrist 51 of the subject is fixed securely in position by the fixing stand 10.

Next, the first band portion 31 is pulled out by a predetermined amount from the fixing stand 10 and the sensor unit 40 is arranged in a position just above the wrist 51 of the subject. In the process, the position of the radial artery 53 is checked beforehand by touch or the like, and the sensor unit 40 is set in such a position that the center of the opening 43 of the base 42 comes to be located above the radial artery 53.

The other end of the first band portion 31 is fixed at one end of the constant force spring 15 arranged in the fixing stand 10. At the other end of the first band portion 31, therefore, a predetermined tension is generated as the result of pulling the first band portion 31 out of the fixing stand 10. By releasing the first band portion 31 from the gripped state, the extraneous part of the first band portion 31 is pulled into the fixing stand 10 by the constant force spring 15. Thus, the first band portion 31 comes to be snugly fitted on the wrist 51 and the housing 11 of the fixing stand 10 without being loosened. In releasing the first band portion 31 from the gripped state, the sensor unit 40 preset in a predetermined position is required to be kept held lightly on the wrist 51 not to displace the sensor unit 40.

Next, as shown in FIG. 4, the second band portion 32 is mounted on the side surface of the fixing stand 10 far from the side surface from which the first band portion 31 has been pulled out. The second band portion 32 is mounted on the fixing stand 10 using a hook-and-loop fastener 14 attached on the side surface of the fixing stand 10 and a hook-and-loop fastener 32a attached on the inner peripheral side at the tip of the other end of the second band portion 32. By engaging the hook-and-loop fasteners 14 and 32a, the second band portion 32 is mounted on the fixing stand 10.

In the process, with the pulse wave measuring apparatus according to this embodiment, as shown in FIG. 5, the hook-and-loop fastener 32a attached on the second band portion 32 and the hook-and-loop fastener 31a attached on the first band portion 31 engage each other through the opening 12 formed in the side surface of the fixing stand 10. Specifically, the hook-and-loop fastener 32a attached on the second band portion 32 engages both the hook-and-loop fastener 14 attached on the fixing stand 10 and the hook-and-loop fastener 31a attached on the first band portion 31. As a result, in the fixed state with the other end of the second band portion 32 mounted on the fixing stand 10, the first band portion 31 is fixed relatively immovably on the fixing stand 10 through the second band portion 32 by the hook-and-loop fasteners 31a and 32a providing the fixing part 33.

As described above, since the first band portion 31 and the second band portion 32 are directly fixed, the wrist 51 is fastened over the whole circumference thereof by the fastening bands 31, 32. Thus, the fastening bands 31, 32 and the wrist 51 are more tightly fastened to each other thereby making it difficult for the fastening bands 31, 32 to loosen. Also, the use of the hook-and-loop fasteners 31a, 32a as the fixing part makes it possible to freely adjust the mounting position of the second band portion 32 on the fixing stand 10 for a greatly improved convenience.

Through the process described above, the mounted state shown in FIG. 6 is realized.

With the above-mentioned configuration of the pulse wave measuring apparatus, the fastening bands 31, 32 can be mounted on the wrist 51 with an appropriate fastening force. This in turn makes it possible to activate by mounting the sensor unit 40 on the wrist 51 under an appropriate pressure. At the same time, the fastening bands 31, 32 can be fastened on the wrist 51 while keeping the wrist 51 fixed in position on the fixing stand 10 in stable fashion. The sensor unit 40 can thus be mounted in an appropriate position on the wrist 51.

Also, the job of mounting the sensor unit 40 is facilitated more than in the prior art, and therefore the sensor unit 40 can be more easily mounted accurately on the wrist 51. Further, with the sensor unit 40 mounted, the fastening bands 31, 32 are loosened less often. It thus becomes difficult for the sensor unit 40 to be displaced, thereby making it possible to measure the pulse wave accurately in stable fashion.

Figure 7:
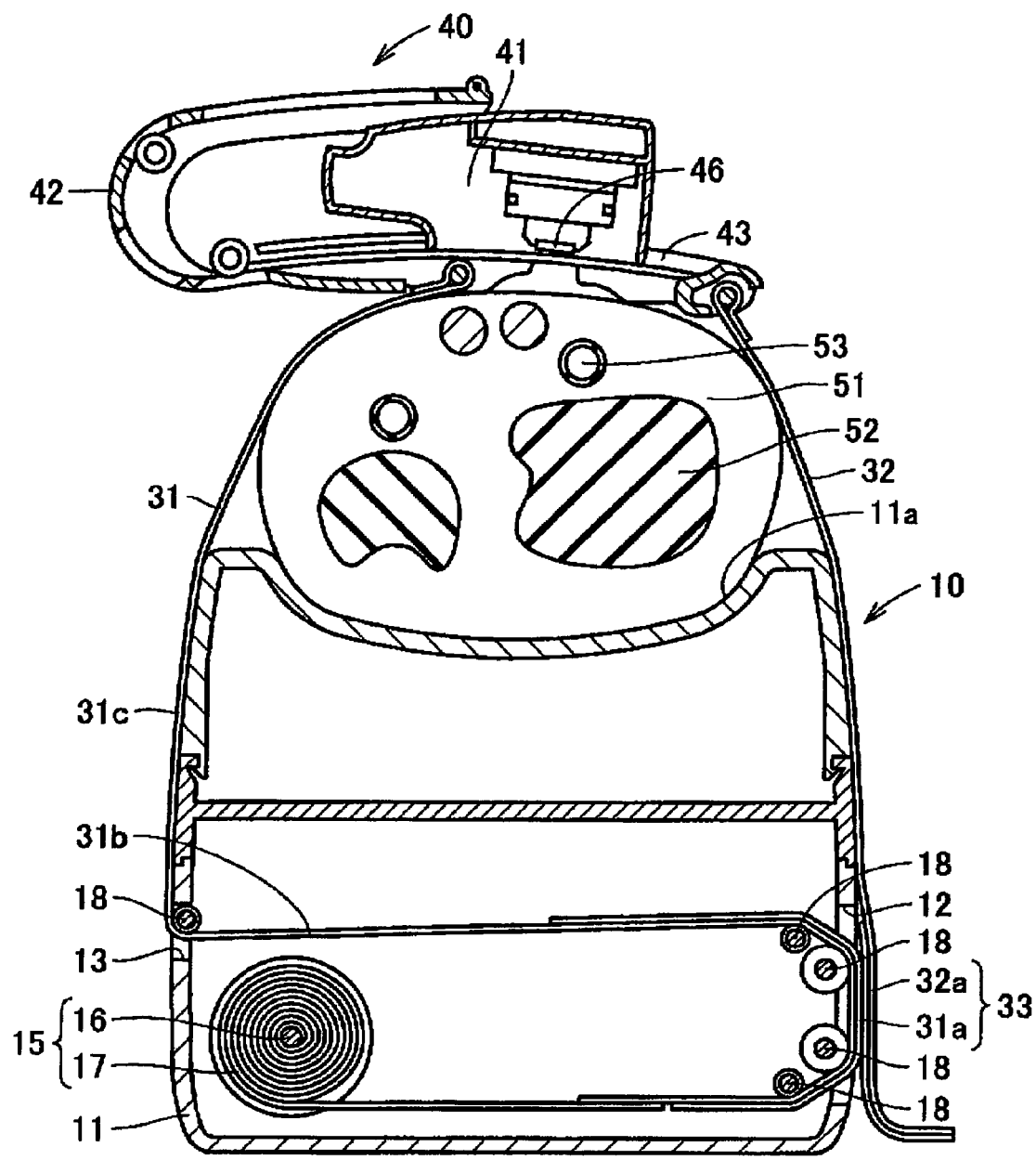
FIG. 7 shows a schematic longitudinal sectional view of a pulse wave measuring apparatus-according to the first embodiment of the invention actually operated to measure the pulse wave.

FIG. 7 is a longitudinal sectional view schematically showing the pulse wave measuring apparatus before actual pulse wave measuring operation. For actual measurement of the pulse wave, as shown in FIG. 7, the case 41 of the sensor unit 40 is slid and arranged in a position where the opening 43 of the base 42 is closed (standby position). The pressure part (such as an air bag) arranged above the pressure sensitive portion 46 is activated. The pressure sensitive portion 46 thus moves down toward the wrist 51 through the opening 43 and is pressed against the wrist 51. As a result, the pulse wave becomes possible to measure by the pressure sensitive part included in the pressure sensitive portion 46.

Second Embodiment

Figure 8:
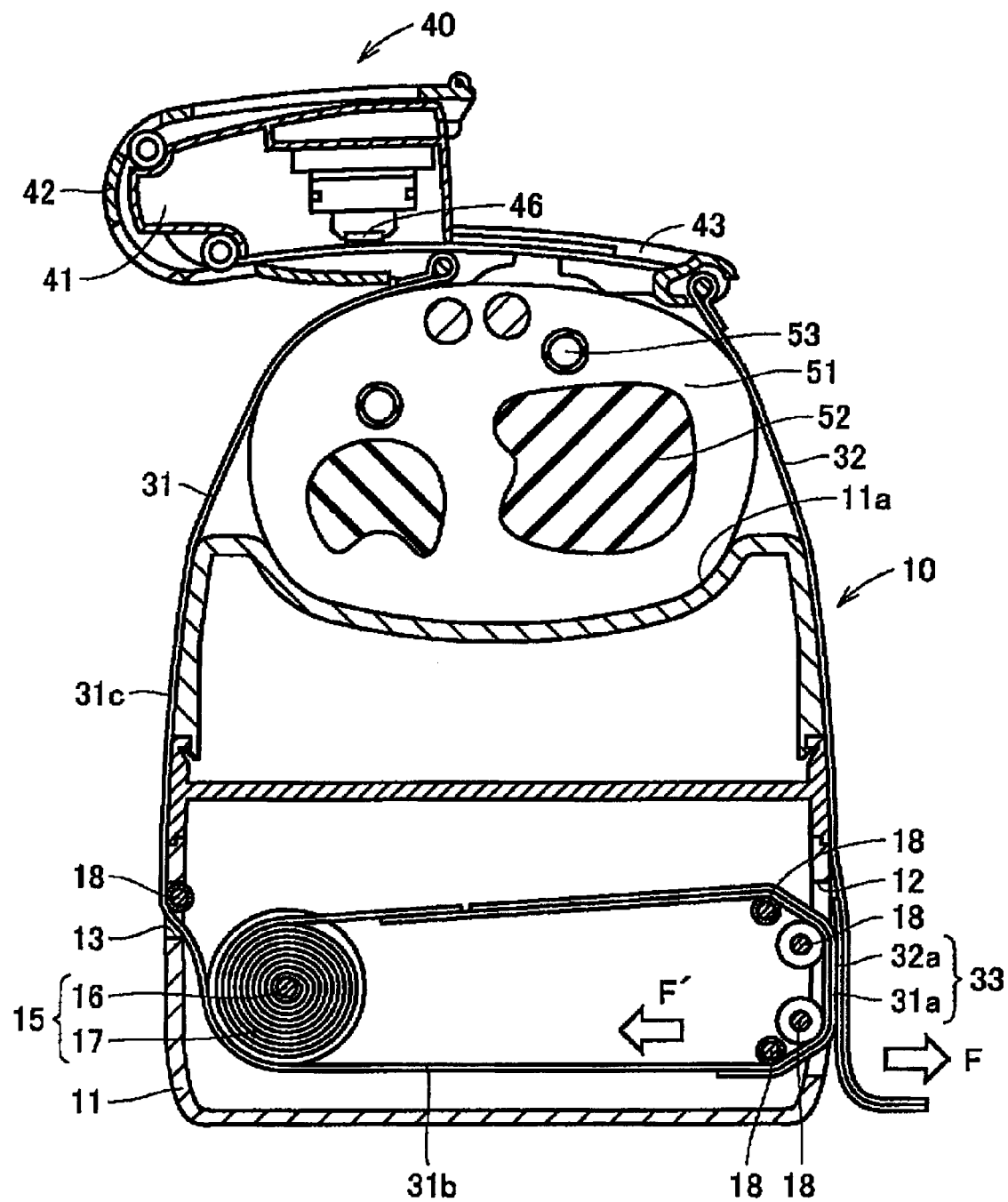
FIG. 8 shows a schematic longitudinal sectional view of the mounted state of a pulse wave measuring apparatus according to a second embodiment of the invention.

FIG. 8 is a longitudinal sectional view schematically showing the mounted state of a pulse wave measuring apparatus according to a second embodiment of the invention. The pulse wave measuring apparatus according to this embodiment is different from the pulse wave measuring apparatus according to the first embodiment described above in the layout of the part of the first band portion accommodated in the fixing stand. In FIG. 8, the component parts identical or similar to the corresponding component parts of the first embodiment are designated by the same reference numerals, respectively, and not explained again.

As shown in FIG. 8, the pulse wave measuring apparatus according to this embodiment, like the pulse wave measuring apparatus according to the first embodiment, comprises a constant force spring 15 as a tensioning part in the housing 11 of the fixing stand 10. The forward end of the spring plate 17 of the constant force spring 15 is fixed to the other end of the first band portion 31. The forward end of the spring plate 17, unlike in the pulse wave measuring apparatus according to the first embodiment, is led out from above the constant force spring 15. The first band portion 31 fixed at the forward end of the spring plate 17 is led out of the fixing stand 10 through the opening 12 formed in one side surface of the housing 11 and the opening 13 formed in the other side surface of the housing 11.

Unlike in the pulse wave measuring apparatus according to the first embodiment, therefore, the part of the first band portion 31 exposed from the opening 12 of the housing 11 has the upper side thereof constituting the other end side fixed to the constant force spring 15 and the lower side thereof constituting the one side fixed to the sensor unit 40. Specifically, as compared with the pulse wave measuring apparatus according to the first embodiment, the part of the first band portion 31 exposed through the opening 12 is inverted vertically.

With this configuration, in the fixed state with the first band portion 31 and the second band portion 32 engaging each other (the state with the wrist fixed by the living organism fixing device) by the hook-and-loop fastener, the first band portion 31 and the second band portion 32 engage each other in such a manner that one end (near to the sensor unit 40) of the first band portion 31 engages the other end (free end side) of the second band portion 32, while the other end (near to the constant force spring 15) of the first band portion 31 engages the one end (near to the sensor unit 40) of the second band portion 32.

With this configuration, in the case where the second band portion 32 is pulled by holding the free end side thereof to separate it from the first band portion 31 as shown in FIG. 8, the force F applied to the free end side of the second band portion 32 and the force F' applied to the first band portion 31 through the sensor unit 40 work in opposite directions at a part engaging the hook-and-loop fasteners 31a, 32a. Even in the case where the second band portion 32 is pulled by the free end side thereof, therefore, the spring plate 17 cannot be pulled out any more from the constant force spring 15. As a result, the second band portion 32 can be smoothly separated from the first band portion 31, thereby providing a pulse wave measuring apparatus high in operability.

In the configuration described above, as shown in FIG. 8, the constant force spring 15 in the unfixed state can be used as a guide part for guiding the first band portion 31 relatively movably with respect to the fixing stand 10. In this case, as the constant force spring 15 is pulled out, the spring plate 17 is rotated in the same direction as the accommodated part 31*b* of the first band portion 31 is pulled out, and therefore no considerable friction is generated between them.

Third Embodiment

Figure 9:
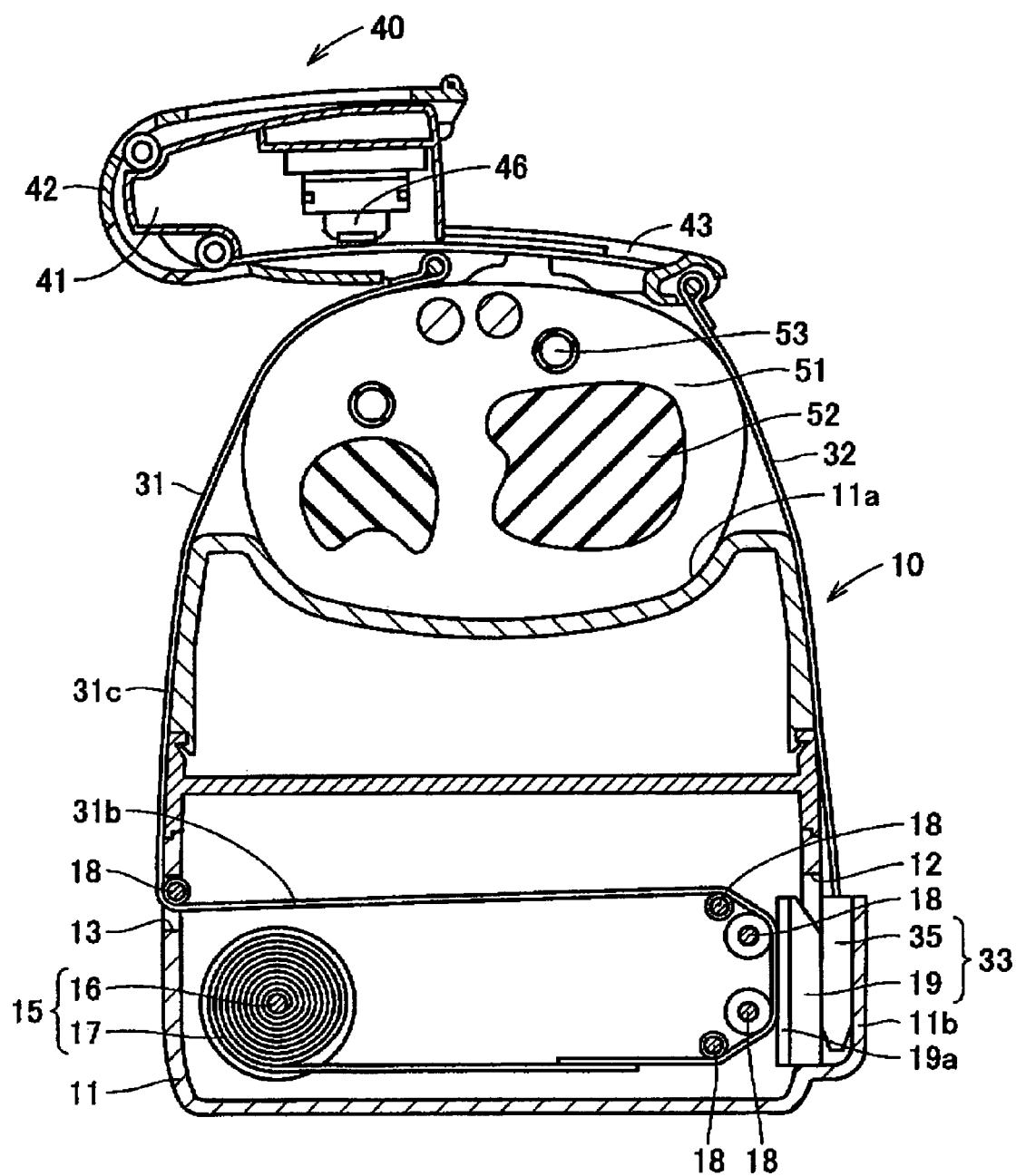
FIG. 9 shows a schematic longitudinal sectional view of the mounted state of a pulse wave measuring apparatus according to a third embodiment of the invention.

FIG. 9 is a longitudinal sectional view schematically showing a pulse wave measuring apparatus according to a third embodiment of the invention. The pulse wave measuring apparatus according to this embodiment, unlike the pulse wave measuring apparatus according the first and second embodiments described above, a brake member is used as a part for fixing the first band portion relatively immovably on the fixing stand with the other end of the second band portion mounted on the fixing stand. The component parts identical or similar to those of the first and second embodiments are designated by the same reference numerals, respectively, and are not described again.

As shown in FIG. 9, the pulse wave measuring apparatus according to this embodiment comprises a buckle 35 at the other end of the second band portion 32. The buckle 35 is formed of a metal, for example, and arranged removably on a receptacle 11*b* arranged on the side surface of the housing 11 of the fixing stand 10. A brake member 19 is slidably arranged inside the receptacle 11*b* of the fixing stand 10. The brake member 19 includes a high friction rubber portion 19*a* on the surface thereof facing the first band portion 31. The brake member 19 is kept energized outward of the housing 11 by a spring not shown. In the pulse wave measuring apparatus according to this embodiment, unlike in the pulse wave measuring apparatus according to the first embodiment, the hook-and-loop fastener is not attached on any of the first band portion 31, the second band portion 32 and the fixing stand 10.

Figure 10A:
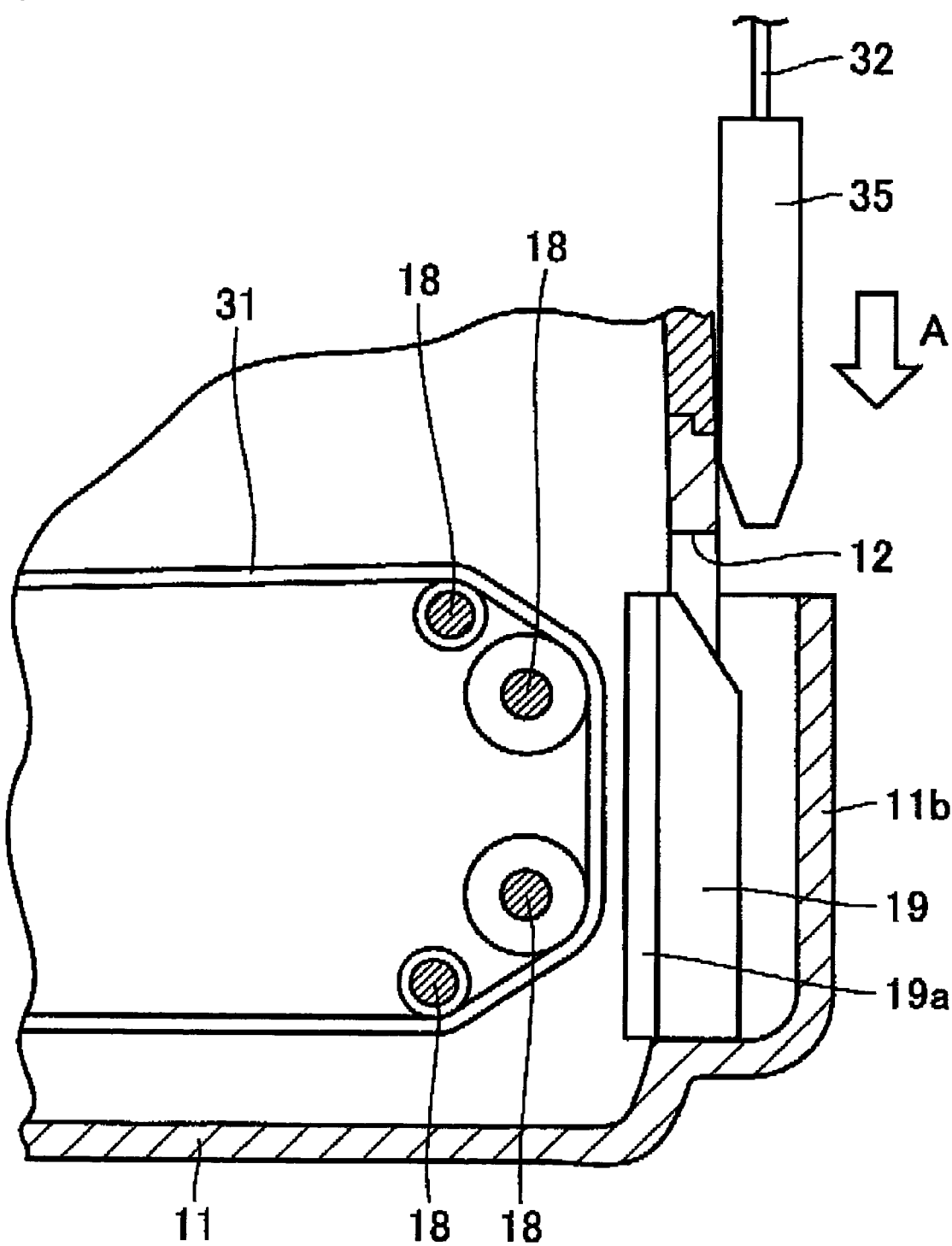
FIG. 10A shows an enlarged sectional view of a mounting portion before the second band portion is mounted on the fixing stand of a pulse wave measuring apparatus according to the third embodiment of the invention.
Figure 10B:
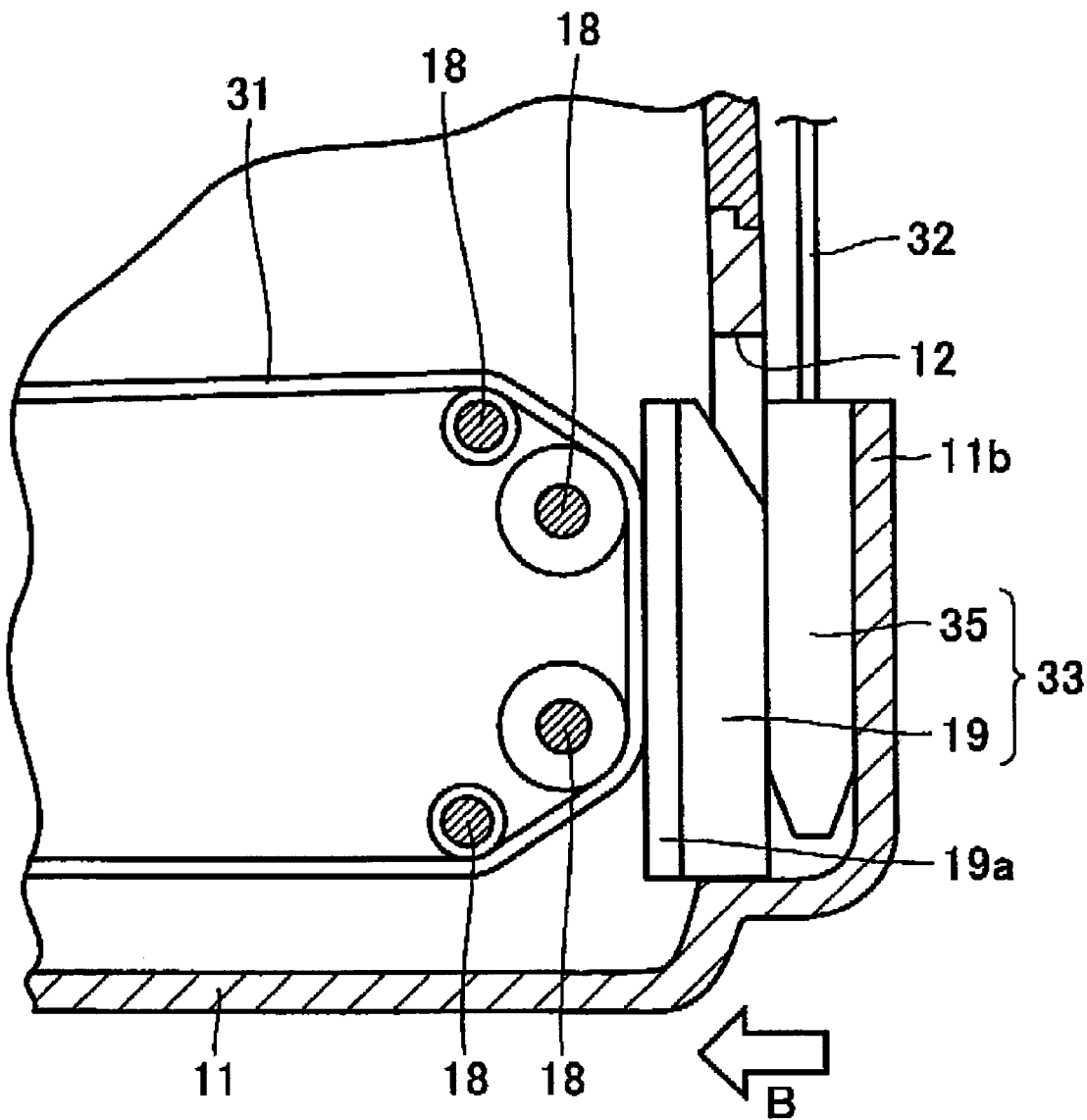
FIG. 10B shows an enlarged sectional view of a mounting portion after the second band portion is mounted on the fixing stand of a pulse wave measuring apparatus according to the third embodiment of the invention.

FIG. 10A is an enlarged sectional view of the mounting portion before the second band portion is mounted on the fixing stand, and FIG. 10B an enlarged sectional view of the mounting portion after the second band portion is mounted on the fixing stand.

As shown in FIG. 10A, in the state where the second band portion 32 is not mounted on the fixing stand 10, i.e. in the unfixed state where the buckle 35 is not inserted in the receptacle 11*b*, the brake member 19 is energized outward of the housing 11 by a spring not shown. As a result, the brake member 19 is not in direct contact with the first band portion 31, and the first-band portion 31 is slidably supported on rollers 18 providing a guide part in the fixing stand 10.

As shown in FIG. 10B, in the fixed state where the buckle 35 is inserted in the receptacle 11*b* in the direction of arrow A, on the other hand, the buckle 35 and the brake member 19 are in direct contact with each other, so that the brake member 19 slides in the direction of arrow B against the energizing force of a spring not shown and comes into contact with the first band portion 31. As a result, the first band portion 31 is held between the rollers 18 and the brake member 19. In the process, the high friction part 19*a* of the brake member 19 is in contact with the first band portion 31 and therefore fixed relatively immovably on the fixing stand 10. Specifically, with the other end of the second band portion 32 mounted on the fixing stand 10, the first band portion 31 is fixed relatively immovably on the fixing stand 10 by the buckle 35 and the brake member 19 providing the fixing part 33.

With this configuration, the first band portion 31 is fixedly pressed against the fixing stand 10 relatively immovably by the brake member 19 in operatively interlocked relation with the process of fixing the second band portion 32 on the fixing stand 10. With the sensor unit 40 mounted, therefore, the fastening bands 31, 32 are not easily loosened, thereby making it possible to measure the pulse wave accurately in stable fashion.

Fourth Embodiment

Figure 11:
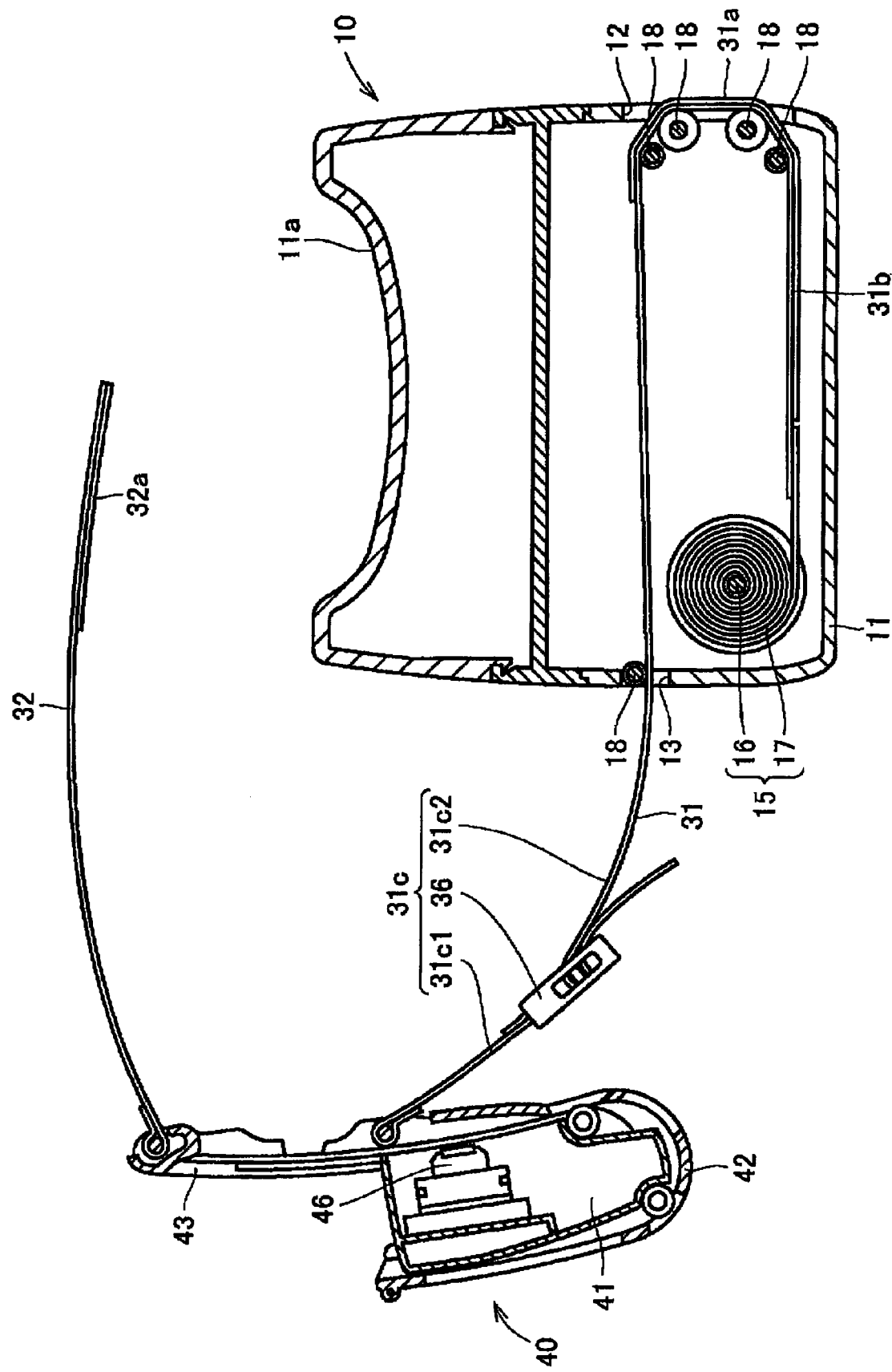
FIG. 11 shows a schematic longitudinal sectional view of the unmounted state of a pulse wave measuring apparatus according to a fourth embodiment of the invention.

FIG. 11 is a longitudinal sectional view schematically showing the unmounted state of a pulse wave measuring apparatus according to a fourth embodiment. The pulse wave measuring apparatus according to this embodiment further comprises a band length adjusting part in the pulse wave measuring apparatus according to the first embodiment. The band length adjusting part is used to correct the length of the fastening bands in accordance with the difference in the position of the radial artery on the left and right wrists or the difference of the wrist of the subject. By adjusting the length of the unaccommodated part of the first band portion pulled out of the fixing stand in advance, an appropriate fastening force is applied to the fastening bands with the sensor unit mounted, while at the same time facilitating the job of mounting the sensor unit on the wrist.

As shown in FIG. 11, with the pulse wave measuring apparatus according to this embodiment, the band length adjusting part is arranged on the unaccommodated part 31*c* of the first band portion 31. The band length adjusting part shown in FIG. 11 is generally called the adjuster. The unaccommodated part 31 of the first band portion 31 is divided into two parts including a sensor unit-side unaccommodated part 31*c*1 and a fixing stand-side unaccommodated part 31*c*2, the ends of which are connected to each other by a connector 36 made of a resin material.

The adjuster is specifically so configured that one end of the connector 36 is fixed at the end of the sensor unit-side unaccommodated part 31*c*1 of the first band portion 31, and the fixing stand-side unaccommodated part 31*c*2 of the first band portion 31 is mounted by being wound on the other end of the connector 36. The fixing stand-side unaccommodated part 31*c*2 mounted at the other end of the connector 36 is folded back so that the bands are closely attached to each other and therefore the length thereof after adjustment is maintained by friction.

The use of the adjuster permits the length of the fixing stand-side unaccommodated part 31*c*2 of the first band portion 31 to be freely adjustable. Thus, the sensor unit can be set in an optimum position of the wrist by simple operation, thereby providing a pulse wave measuring apparatus of high operability.

Fifth Embodiment

Figure 12:
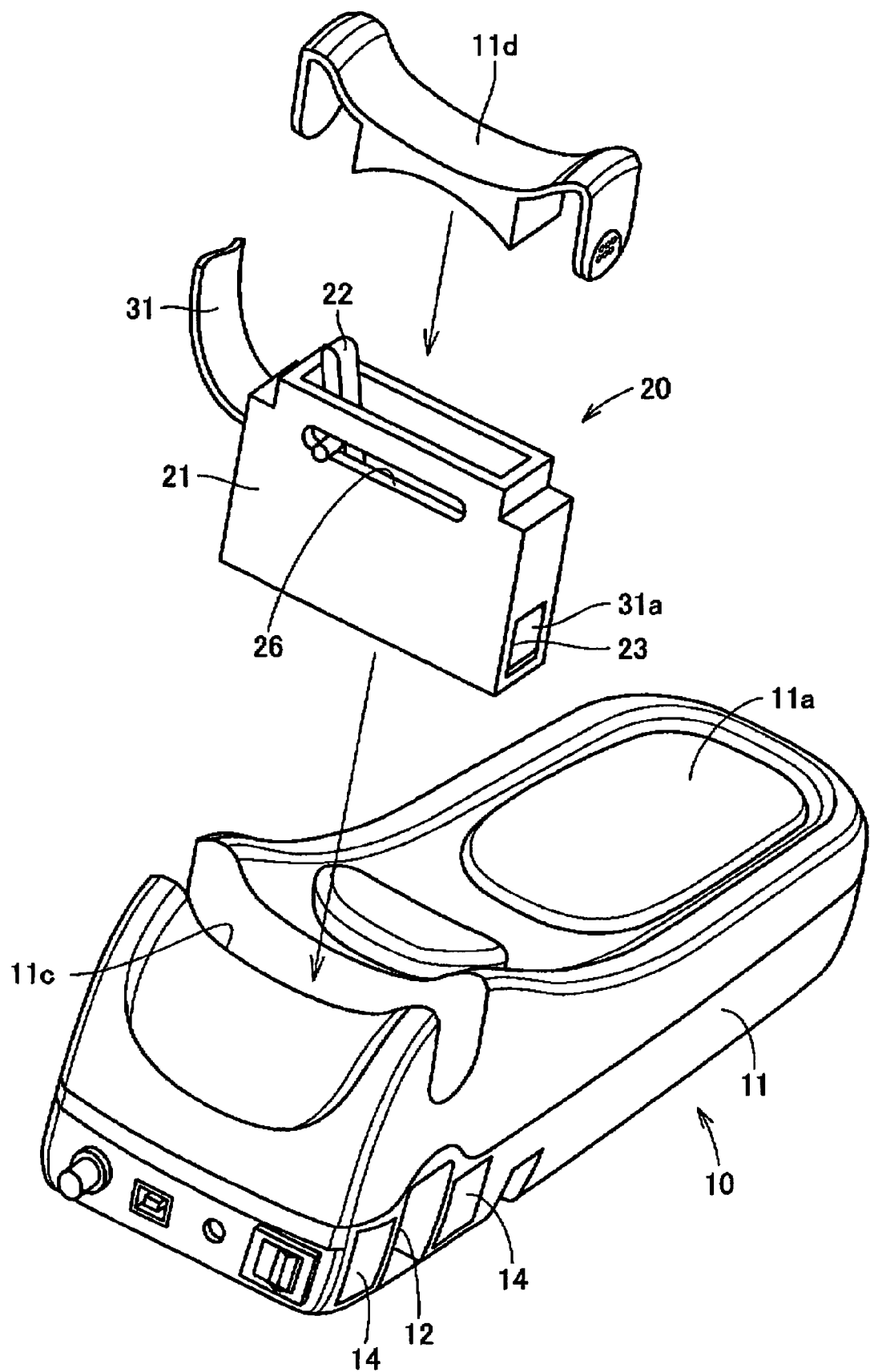
FIG. 12 shows an exploded perspective view of the structure of the fixing stand of a pulse wave measuring apparatus according to a fifth embodiment of the invention.
Figure 13:
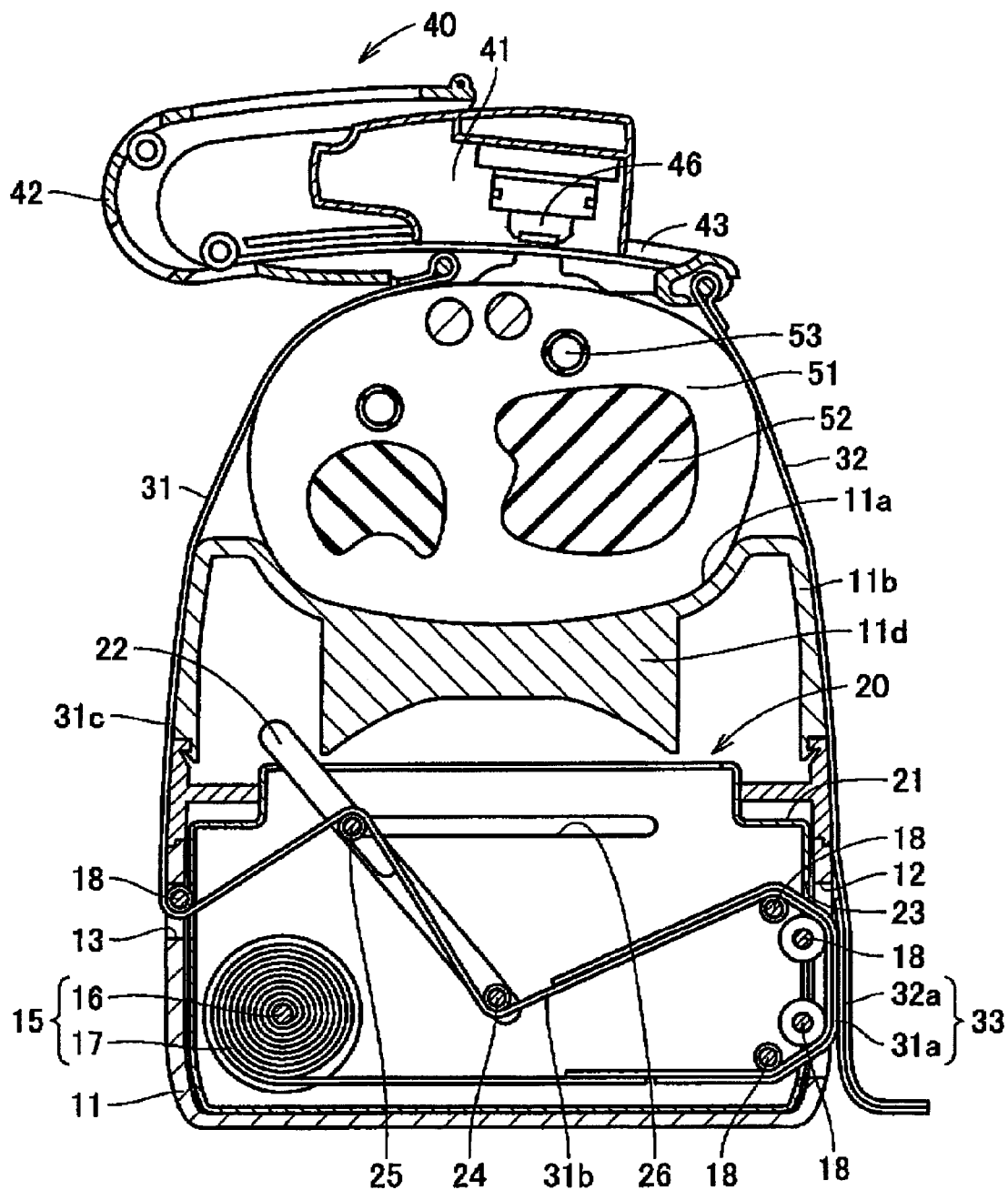
FIG. 13 shows a schematic longitudinal sectional view of a pulse wave measuring apparatus according to the fifth embodiment of the invention as applied to the left arm wrist as an object portion.
Figure 14:
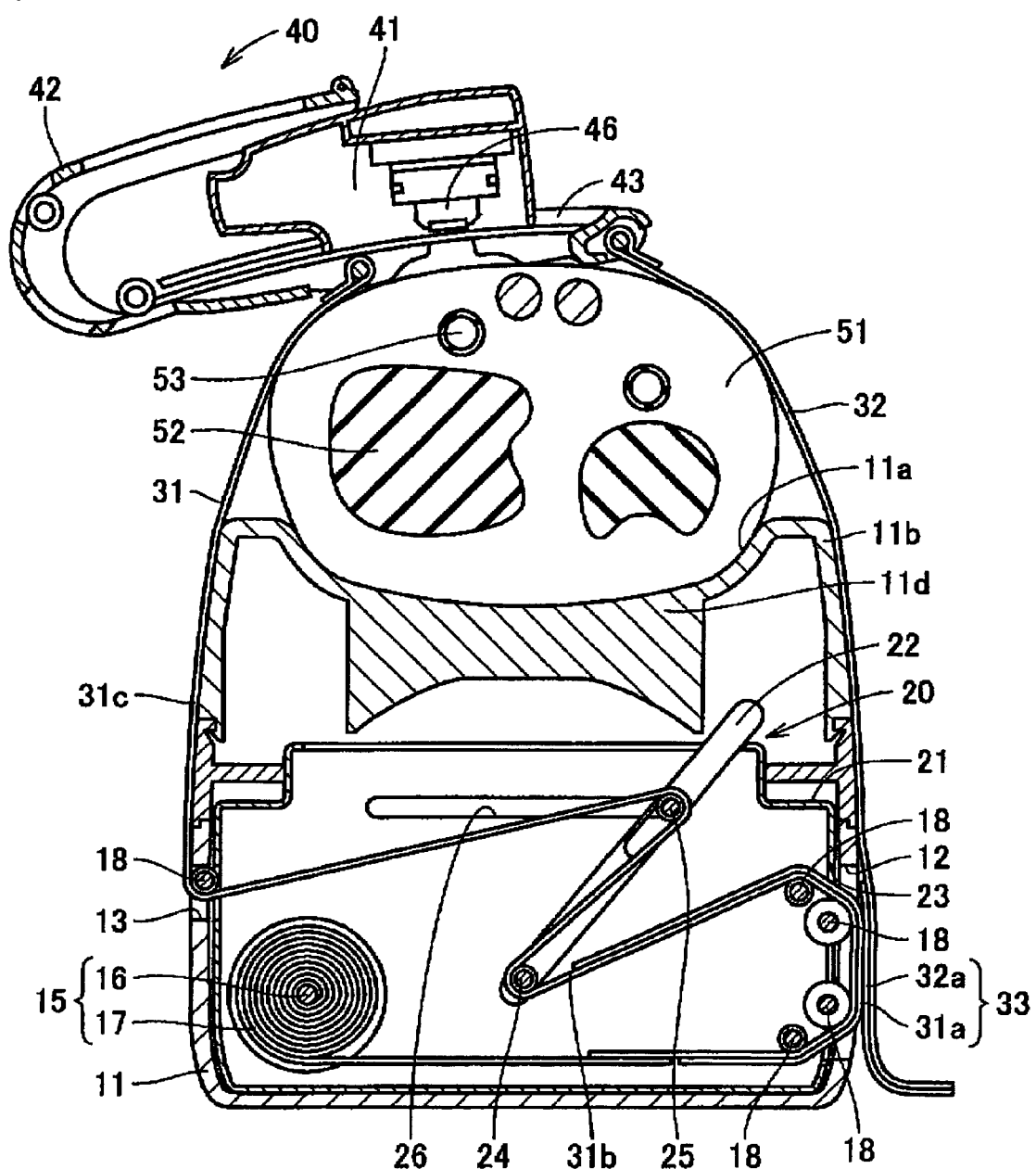
FIG. 14 shows a schematic longitudinal sectional view of a pulse wave measuring apparatus according to the fifth embodiment of the invention as applied to the right arm wrist as an object portion.
Figure 15:
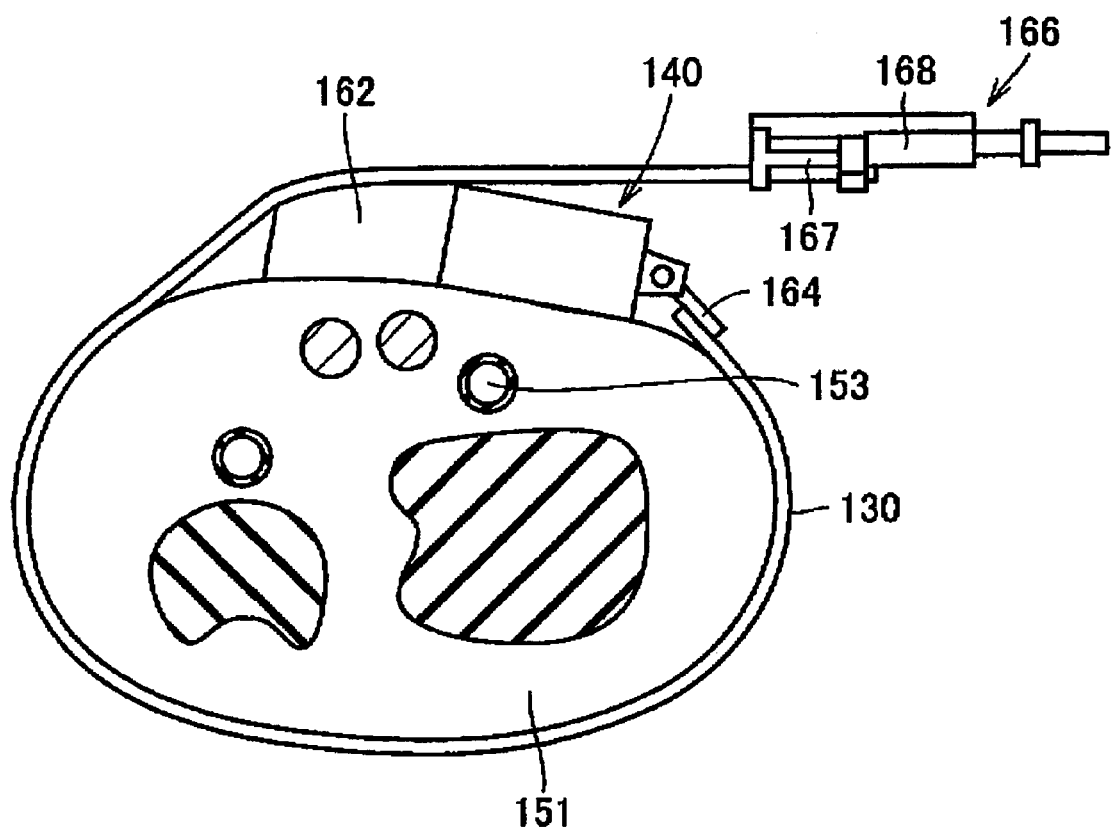
FIG. 15 shows a longitudinal sectional view of an example of the structure of the conventional pulse wave measuring apparatus as mounted on a living organism.

FIG. 12 is an exploded perspective view showing the configuration of the fixing stand of a pulse wave measuring apparatus according to the third embodiment of the invention. FIGS. 13 and 14 are longitudinal sectional views schematically showing a pulse wave measuring apparatus according to this embodiment, of which FIG. 13 is a diagram showing a case in which the wrist of the left arm is used as an object portion, and FIG. 14 a case in which the wrist of the right arm is used as an object portion. In this embodiment, the component parts similar or identical to those of the first to fourth embodiments described above are designated by the same reference numerals, respectively, and not described again.

The pulse wave measuring apparatus according to this embodiment, in addition to the component parts of the pulse wave measuring apparatus according to the first embodiment, further comprises a band length adjusting part. The band length adjusting part is used to correct the length of the fastening bands appropriately in accordance with the position difference of the radial artery in the left and right wrists or the difference of the wrist size of the subject. By adjusting the length of the unaccommodated part of the first band portion pulled out of the fixing stand in advance, an appropriate fastening force is applied to the fastening bands with the sensor unit mounted, while at the same time facilitating the job of mounting the sensor unit on the wrist.

As shown in FIG. 12, with the pulse wave measuring apparatus according to this embodiment, an opening 11c is formed in the upper surface of the housing 11 of the fixing stand 10, and through this opening 11c, a band length adjusting mechanism 20 providing the band length adjusting part is fitted in the fixing stand 10. Specifically, in the pulse wave measuring apparatus according to this embodiment, unlike in the pulse wave measuring apparatus according to the fourth embodiment, the band length adjusting part is arranged on the fixing stand 10. Incidentally, the opening 11c formed in the upper surface of the fixing stand 10 is covered by a lid 11d.

The band length adjusting mechanism 20 mainly includes a casing 21 and a rotary lever 22 providing a rotary member assembled rotatably on the casing 21. The rotary lever 22 has one end thereof journaled immovably on the casing 21 by a fixed shaft 24, and the other end thereof mounted. rotatably by a movable shaft 25 (FIG. 13). The movable shaft 25 is adapted to move horizontally under the guide of a slit 26 formed in the casing 21.

A constant force spring 15 is arranged in the band length adjusting mechanism 20, and the other end of the first band portion 31 is fixed at one end of the constant force spring 15. The first band portion 31 is guided by a plurality of rollers 18 providing a guide part in such a manner as to be partially exposed through the opening 23 formed in the side surface of the casing 21. The first band portion 31 is adapted to slidably engage the movable shaft 25 and the fixed shaft 24 for rotatably assembling the rotary lever 22 on the casing 21, and pulled out of the casing 21 from the side surface far from the side surface formed with the opening 23.

In the pulse wave measuring apparatus having the configuration described above, the difference between the length of the unaccommodated part 31c of the first band portion 31 required when the wrist of the left arm of the subject is used as an object portion as shown in FIG. 13 on the one hand and the length of the unaccommodated part 31c of the first band portion 31 required when the wrist of the right arm of the subject is used as an object portion as shown in FIG. 14 on the other hand, is absorbed by the accommodated part 31b of the first band portion 31 accommodated in the fixing stand 10 by operating the rotary lever 22. With the configuration of this pulse wave measuring apparatus, therefore, the length of the unaccommodated part 31c of the first band portion 31 can be properly adjusted by rotating the rotary lever 22. In this way, the sensor unit can be mounted in simplistic fashion.

In the case where the band length adjusting mechanism 20 is lacking, the stroke of pulling out the constant force spring 15 would be limited by the width of the housing 11 of the fixing stand 10. As a result, a sufficiently proper fastening force may not be applied which otherwise could be secured by selecting the right arm wrist or the left arm wrist of the subject as an object portion or according to the wrist size of the subject. In such a case, if a positively proper fastening force is to be applied, the width of the fixing stand 10 is required to be further increased to secure a sufficiently long stroke of pulling out the constant force spring 15, which would make an undesirably bulky apparatus. With the pulse wave measuring apparatus having the configuration described above, on the other hand, the length of the unaccommodated part 31c of the first band portion 31 can be freely adjusted without regard to the amount in which the constant force spring 15 is pulled out, and therefore the convenience is remarkably improved while at the same time contributing to a reduced size of the apparatus.

Incidentally, the pulse wave measuring apparatus having the configuration described above employs the casing 21 and the lid 11d as a band length maintaining part for maintaining the length of the unaccommodated part 31c of the first band portion 31 after adjustment. Specifically, the rotary lever 22 is held fixedly between the casing 21 and the lower end of the lid 11d, thereby preventing the unintentional rotation of the rotary lever 22 which otherwise might be caused by the operation of pulling out the first band portion 31. As a result, the length of the unaccommodated part 31c of the first band portion 31 can be adjusted to secure one of the two states shown in FIGS. 13 and 14, thereby providing a very convenient pulse wave measuring apparatus.

According to the first to fifth embodiments, the fastening bands are divided into two independent band portions including the first band portion and the,second band portion (in the fourth embodiment, the unaccommodated part of the first band portion is further divided into two parts including the sensor unit-side unaccommodated part and the fixing stand-side unaccommodated part, which are connected by a connector, resulting in a total of three independent bands). Nevertheless, the invention is not specifically limited to these configurations, but may comprise one fastening band with the sensor unit slidably mounted thereon. In such a case, the first band portion and the second band portion each represent an integrated part of a single band.

Also, according to the first to fifth embodiments, a constant force spring configured of a spiral spring is employed as an example of the tensioning part. The invention, however, is not specifically limited to such a spring, but can employ any device capable of pulling the other end of the first band portion with a predetermined force.

The band length adjusting part included in the fourth embodiment and the band length adjusting part include in the fifth embodiment may both be included in a pulse wave measuring apparatus. In this case, preferably, the band length adjusting part according to the fifth embodiment is used mainly for switching the right and left hands, and the band length adjusting part according to the fourth embodiment is used for fine adjustment.

In the fifth embodiment, a configuration is shown as an example in which the band length can be adjusted two ways to the states shown in FIGS. 13 and 14. Nevertheless, the invention is not specifically confined to this configuration, and more preferably, the band length is adjustable in several steps in accordance with the distance covered by the rotary lever.

Further, in the first to fifth embodiments, a pulse wave measuring apparatus using the wrist as an object portion is illustrated. The application of the pulse wave measuring apparatus according to the invention is not limited to the use of the wrist, but an upper arm or a finger may be equally used as an object portion.

As described above, the embodiments disclosed herein are illustrative but not limitative in all respects. The technical scope of the invention is defined by the claims appended hereto, and includes all modifications without departing from the spirit and scope equivalent to those contained in the description of the claims.

What is claimed is:

1. A pulse wave measuring apparatus comprising a sensor unit having a pressure sensitive portion and a living organism fixing device adapted for fixing a living organism:

wherein the living organism fixing device includes a fixing stand for fixing the living organism in position, and at least a fastening band for connecting the fixing stand and the sensor unit to each other and fixedly fastening the living organism fixedly to the fixing stand while at the same time activating by pressing the sensor unit against the living organism;

wherein the pressure sensitive portion is pressed against the living organism thereby to measure the pulse with the living organism fixed by the living organism fixing device;

wherein the fastening band includes a first band portion with one end mounted on the sensor unit and the other end mounted on the fixing stand, and a second band portion with one end mounted on the sensor unit and the other end removably mounted on the fixing stand; and wherein the fixing stand includes a tensioning part for automatically pulling the other end of the first band portion with a predetermined force.

2. The pulse wave measuring apparatus according to claim 1, further comprising a fixing part for fixing the first band portion relatively immovably on the fixing stand with the other end of the second band portion mounted on the fixing stand.

3. The pulse wave measuring apparatus according to claim 2, wherein the fixing part includes a hook-and-loop fastener arranged on the first band portion and the second band portion, and wherein the first band portion and the second band portion are caused to engage each other by the hook-and-loop fastener thereby to fix the first band portion on the fixing stand relatively immovably.

4. The pulse wave measuring apparatus according to claim 3, wherein the one end of the first band portion engages the other end of the second band portion and the other end of the first band portion engages the one end of the second band portion at the positions where the first band portion and the second band portion are caused to engage each other by the hook-and-loop fastener.

5. The pulse wave measuring apparatus according to claim 2, wherein the fixing part is configured of a brake member operatively interlocked with a fastener on the second band portion, and wherein the second band portion is mounted on the fixing stand so that the brake member is brought into contact with the first band portion and the first band portion is fixedly pressed against the fixing stand relatively immovably.

6. The pulse wave measuring apparatus according to any one of claims 1 to 5, wherein the tensioning part is accommodated in the fixing stand, wherein the first band portion includes an accommodated part located in the fixing stand and an unaccommodated part located outside the fixing stand; and wherein the first band portion is guided relatively movably with respect to the fixing stand by a guide part arranged in the fixing stand with the living organism unfixed by the living organism fixing device.

7. The pulse wave measuring apparatus according to claim 6, wherein the guide part is configured of at least a roller arranged on the sliding parts of the fixing stand and the first band portion.

8. The pulse wave measuring apparatus according to claim 6, further comprising a band length adjusting part for adjusting the length of the unaccommodated part of the first band portion.

9. The pulse wave measuring apparatus according to claim 8, wherein the band length adjusting part is arranged on the unaccommodated part of the first band portion.

10. The pulse wave measuring apparatus according to claim 8, wherein the band length adjusting part is arranged on the fixing stand.

11. The pulse wave measuring apparatus according to claim 10, wherein the band adjusting part includes a band length maintaining part for maintaining a predetermined length of the unaccommodated part of the first band portion after adjustment.

12. The pulse wave measuring apparatus according to claim 10, wherein the band length adjusting part includes a rotary member having one end journaled and the other end rotatable, wherein the first band portion slidably engages a fixed shaft and a movable shaft arranged on the one end and the other end, respectively, of the rotary member, and wherein the length of the unaccommodated part of the first band portion is adjusted by rotating the rotary member.

13. The pulse wave measuring apparatus according to claim 6, wherein the tensioning part is a constant force spring.

* * * * *